US012770484B2

(12) United States Patent
Thompson et al.

(10) Patent No.: US 12,770,484 B2
(45) Date of Patent: Oct. 20, 2026

(54) MITIGATING VIOLENCE IN A CLINICAL CARE ENVIRONMENT

(71) Applicant: Hill-Rom Services, Inc., Batesville, IN (US)

(72) Inventors: Autumn S. Thompson, Philadelphia, PA (US); Stacie L. Brough, Syracuse, NY (US); Kathryn Piston, Syracuse, NY (US); David E. Quinn, Moravia, NY (US); Daniel C. Shirley, Raleigh, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 14 days.

(21) Appl. No.: 18/810,689

(22) Filed: Aug. 21, 2024

(65) Prior Publication Data

US 2025/0087074 A1 Mar. 13, 2025

Related U.S. Application Data

(60) Provisional application No. 63/581,485, filed on Sep. 8, 2023.

(51) Int. Cl.
*G08B 21/02* (2006.01)
*A61B 90/90* (2016.01)

(52) U.S. Cl.
CPC .............. *G08B 21/02* (2013.01); *A61B 90/90* (2016.02)

(58) Field of Classification Search
CPC .......... G08B 21/02; G08B 21/22; A61B 90/90
See application file for complete search history.

(56) References Cited

U.S. PATENT DOCUMENTS

| | | | |
|---|---|---|---|
| 5,747,719 | A | 5/1998 | Bottesch |
| 9,002,944 | B2 | 4/2015 | Lewis et al. |
| 9,728,077 | B1 | 8/2017 | Fu et al. |
| 9,749,825 | B2 | 8/2017 | Payne et al. |
| 9,872,148 | B2 | 1/2018 | King et al. |
| 10,616,396 | B2 | 4/2020 | Gersten |
| 10,796,396 | B2 | 10/2020 | Braun et al. |
| 10,964,177 | B1 | 3/2021 | Coles |

(Continued)

FOREIGN PATENT DOCUMENTS

| | | | |
|---|---|---|---|
| CA | 2595830 | A1 | 2/2009 |
| WO | 2020213058 | A1 | 10/2020 |

OTHER PUBLICATIONS

Kelen, Gabor D., et al. "Hospital-Based Shootings in the United States: 2000 to 2011." Annals of Emergency Medicine, 2012, https://doi.org/10.1016/j.annemergmed.2012.08.012.

*Primary Examiner* — Quan Zhen Wang
*Assistant Examiner* — Rajsheed O Black-Childress
(74) *Attorney, Agent, or Firm* — Merchant & Gould P.C.

(57) ABSTRACT

A system for mitigating violence in a clinical care environment. The system detects at least one individual who is exhibiting violent behavior. The system identifies a location of the at least one individual who is exhibiting the violent behavior based on data received from a location tracking system. The system controls operation of a first device based on the location of the at least one individual who is exhibiting the violent behavior, The system generates an alert based on the location of the at least one individual who is exhibiting the violent behavior, the alert communicated to a second device associated with a caregiver in the clinical care environment.

18 Claims, 11 Drawing Sheets

(56) References Cited

U.S. PATENT DOCUMENTS

| | | | |
|---|---|---|---|
| 11,382,511 B2 | 7/2022 | Tunnell et al. | |
| 11,545,012 B2 | 1/2023 | Connell, II et al. | |
| 2008/0126132 A1* | 5/2008 | Warner | G16H 10/60 705/3 |
| 2010/0156630 A1 | 6/2010 | Ainsbury | |
| 2015/0213207 A1* | 7/2015 | Amarasingham | G16H 50/50 705/2 |
| 2019/0080577 A1* | 3/2019 | Raz | G01H 3/10 |
| 2021/0100481 A1 | 4/2021 | Abdel-Malek et al. | |
| 2021/0193336 A1 | 6/2021 | Nemeth | |
| 2022/0189266 A1 | 6/2022 | Millar et al. | |

* cited by examiner

MITIGATING VIOLENCE IN A CLINICAL CARE ENVIRONMENT

BACKGROUND

Healthcare facilities are vulnerable to gun violence because they are publicly accessible and often treat victims who were previously involved in violent attacks. Gun violence within healthcare facilities is particularly dangerous because healthcare facilities often treat large quantities of patients, and many patients have physical limitations that inhibit their ability to escape or defend themselves. Furthermore, patients and caregivers may become anxious and scared within the clinical care environment when faced with the possibility of gun violence, which may interfere with their ability to reach safety and help others.

SUMMARY

In general terms, the present disclosure relates to detecting a potentially violent disturbance within a clinical care environment. In one possible configuration, an alert is generated when a violent disturbance is detected, the alert including a recommendation for reaching a safe location within the clinical care environment. Various aspects are described in this disclosure, which include, but are not limited to, the following aspects.

One aspect relates to a system for detecting violence in a clinical care environment. The system includes at least one processing device and a memory device. The memory device stores instructions which, when executed by the at least one processing device, cause the at least one processing device to: detect at least one individual who is exhibiting violent behavior within the clinical care environment; identify a location of the at least one individual who is exhibiting the violent behavior based on data received from a location tracking system; control operation of a first device based on the location of the at least one individual who is exhibiting the violent behavior; the first device being located within the clinical care environment; and generate an alert based on the location of the at least one individual who is exhibiting the violent behavior, the alert being communicated to a second device associated with a caregiver on duty within the clinical care environment.

Another aspect relates to a method of detecting violence in a clinical care environment. The method includes detecting at least one individual who is exhibiting violent behavior within the clinical care environment; identifying a location of the at least one individual who is exhibiting the violent behavior based on data received from a location tracking system; controlling operation of a first device based on the location of the at least one individual who is exhibiting the violent behavior; the first device being located within the clinical care environment; and generating an alert based on the location of the at least one individual who is exhibiting the violent behavior, the alert being communicated to a second device associated with a caregiver on duty within the clinical care environment.

Another aspect relates to a non-transitory computer readable storage medium storing instructions, which when executed by a computing device, causes the computing device to receive an alert that a violent individual is located within a clinical care environment. Furthermore, the instructions, which when executed by a computing device, cause the computing device to receive a recommendation for guiding a user to a safe location by avoiding the violent individual identified within the alert, wherein the recommendation includes at least one of an exit plan and a hiding plan displayed on a map of the clinical care environment. Further yet, the instructions, which when executed by a computing device, cause the computing device to receive updates to the map of the clinical care environment, wherein the updates include one or more changes to the exit plan or the hiding plan based on a real-time location of the violent individual within the clinical care environment.

A variety of additional aspects will be set forth in the description that follows. The aspects can relate to individual features and to combinations of features. It is to be understood that both the foregoing general description and the following detailed description are exemplary and explanatory only and are not restrictive of the broad inventive concepts upon which the examples disclosed herein are based.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
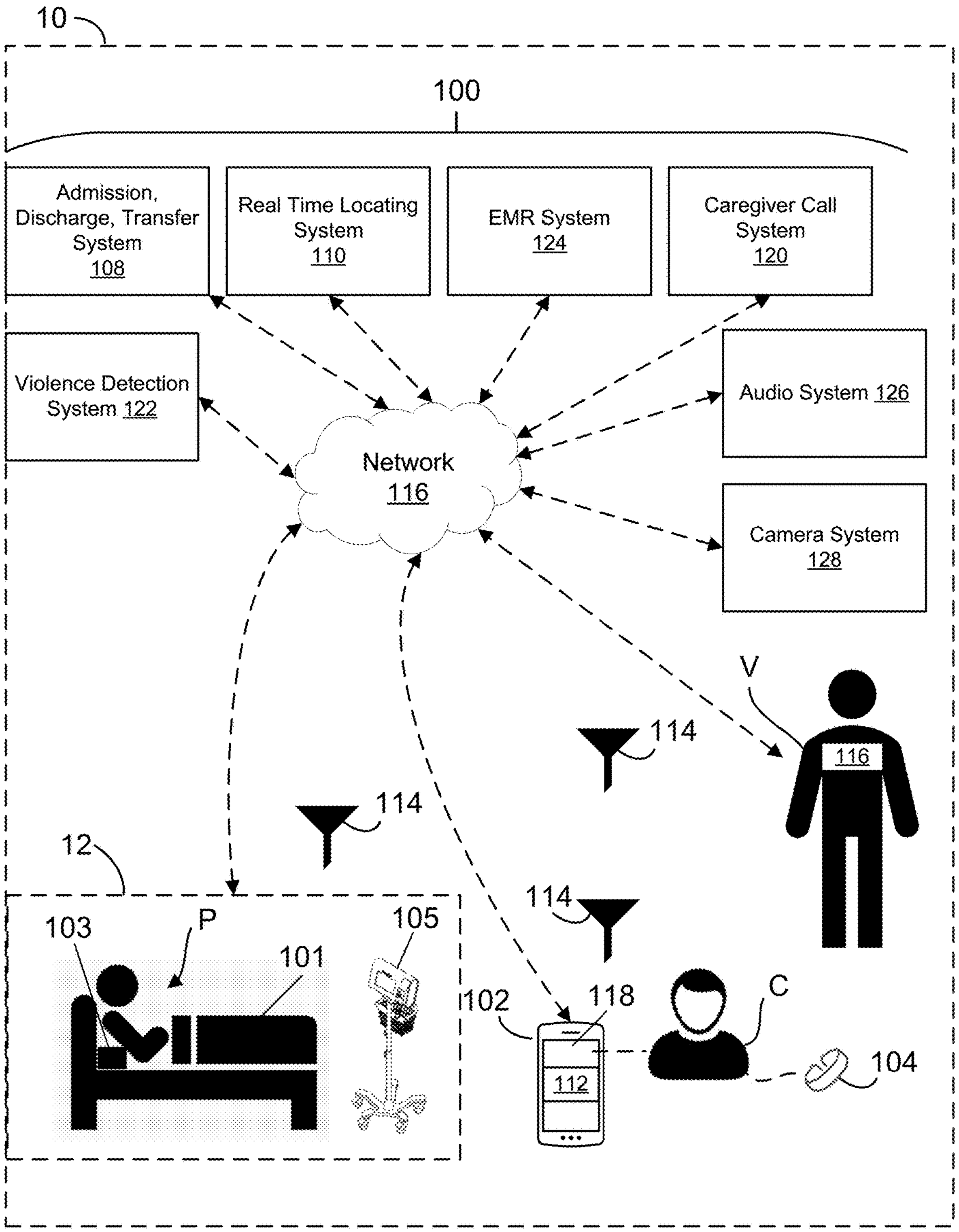
FIG. 1 schematically illustrates an example of a clinical care environment that includes a detection system for detecting disturbances within the clinical care environment.

FIG. 1 schematically illustrates a clinical care environment 10 that includes a detection system 122 for detecting one or more individuals who are exhibiting violent behavior among a plurality of individuals within the clinical care environment 10. Furthermore, the detection system 122 is configured to identify and track the locations of the one or more individuals who are exhibiting the violent behavior, and to issue an alert that includes recommendations based on the locations of the one or more individuals who are exhibiting the violent behavior within the clinical care environment 10. Further yet, the detection system 122 is configured to generate the recommendations based on data from one or more clinical care environment systems 100 including, without limitation, an admission, discharge, transfer (ADT) system 108, a real-time locating system (RTLS) 110, and electronic medical record (EMR) system 124, a caregiver call system 120, an audio system 126, and a camera system 128, each of which will be described in more detail below.

In certain examples, the clinical care environment 10 is a clinical care environment such as a hospital, a nursing home, a rehabilitation center, a long-term care facility, and the like. In certain examples, and as shown in FIG. 1, individuals within the clinical care environment 10 who are not exhibiting violent behavior (also referred to as non-violent individuals) include one or more patients P and one or more caregivers C. As shown in FIG. 1, a patient P is located in a patient environment 12, which can include a room or other designated area within the clinical care environment 10. For example, the patient environment 12 can include a patient room, a department (e.g., emergency department), a clinic, a ward, or other area within the clinical care environment 10. Furthermore, the patient environment 12 can include one or more devices for monitoring the patient and providing information to the patient, such as a spot monitor 105.

One or more caregivers C carry a communications device 102 on which the caregiver may receive alerts and/or recommendations from the detection system 122. Examples of the communications devices 102 can include smartphones, tablet computers, or other type of portable computing devices. In further examples, the communications devices 102 can include workstation computers. In some examples, a communication application 112 can be downloaded on the communications devices 102 to facilitate communication between the caregiver C and the detection system 122. In further examples, the communication application 112 can be a web-based or cloud-based application that is accessible on the communications devices 102.

In certain examples, the detection system 122 can provide communication channels allowing the caregivers C, administrators, or patients P to leave video, audio, or text messages to communicate during an emergency or discuss a patient's condition. As discussed below with reference to FIGS. 5-8, a patient's condition can influence an exit plan that is created by the detection system 122 for the patient P. In some examples, the detection system 122 is an extension of the Voalte® platform available from Hillrom®. In certain examples, the communication application 112 incorporates elements of the systems and methods described in U.S. Pat. No. 9,749,825, granted Aug. 29, 2017, titled Connection-Oriented Messaging and Signaling in Mobile Health Networks, and U.S. Pat. No. 9,872,148, granted Jan. 16, 2018, titled Adaptive Mobile Wireless Call Rescue, which are incorporated herein in their entireties.

Data that is collected from the one or more clinical care environment systems 100 within the clinical care environment 10 can be transmitted to the detection system 122 across a communications network 116. As shown in FIG. 1, the communications devices 102 used by the caregivers C are all connected to the communications network 116. The communications network 116 can include any type of wired or wireless connections or any combinations thereof. Examples of wireless connections include Wi-Fi, Bluetooth, and broadband cellular networks including 4G or 5G. In some examples, the communications network 116 includes a broadband cellular network. In some examples the communications network 116 includes the Internet.

Figure 2:
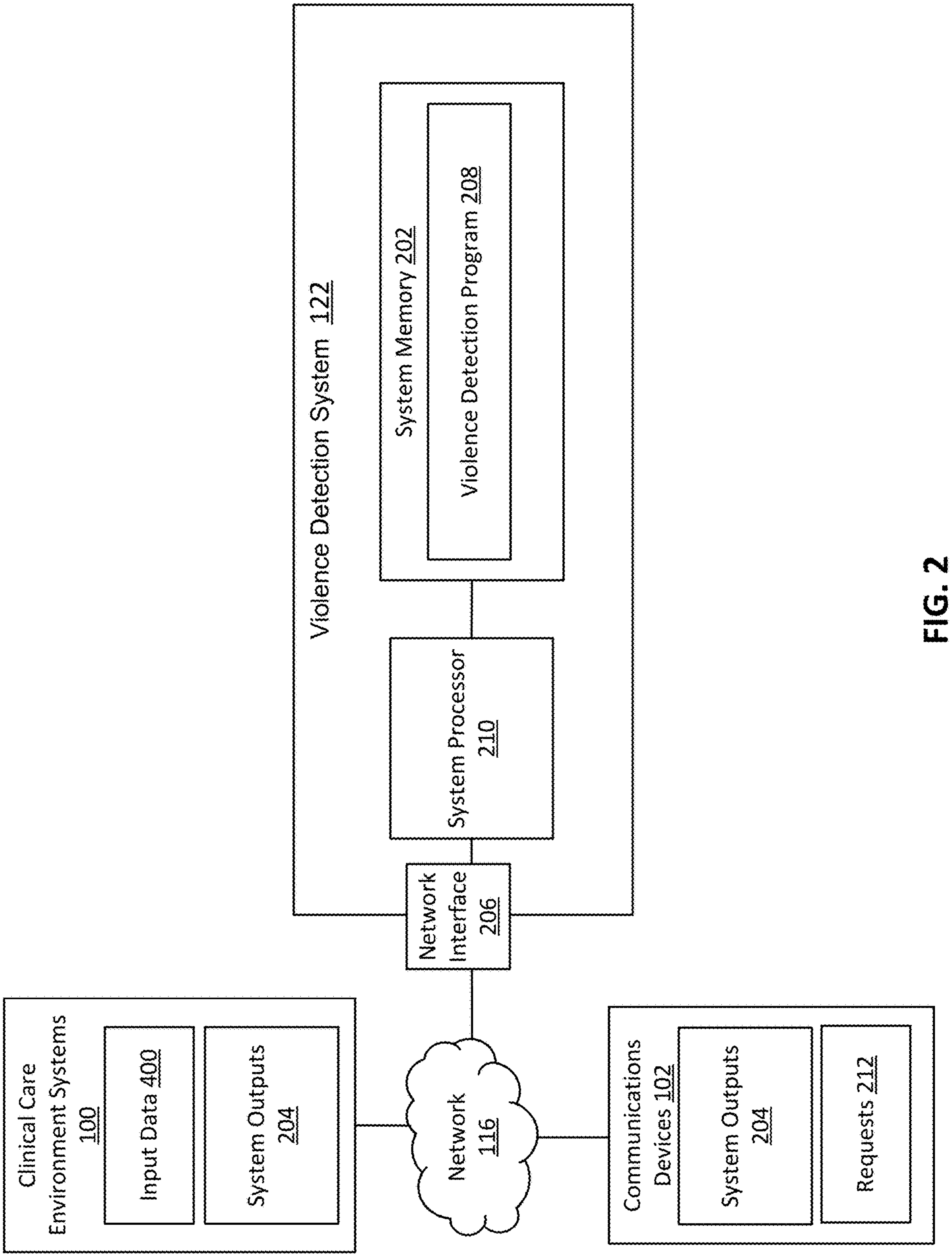
FIG. 2 schematically illustrates an example of the detection system of FIG. 1.
Figure 4:
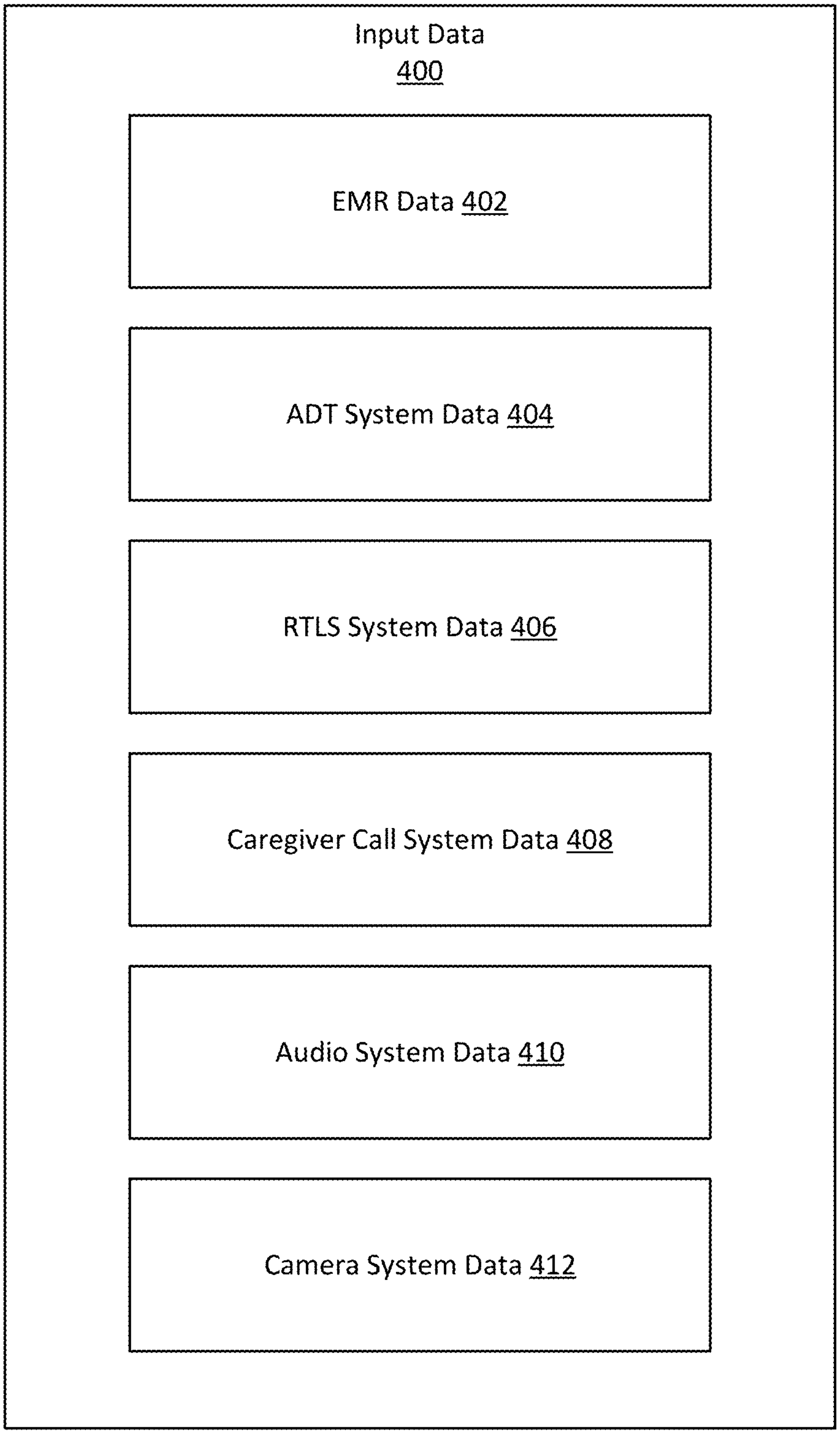
FIG. 4 schematically illustrates examples of input data generated by one or more data sources included in the clinical care environment of FIG. 1.

In certain examples, the detection system 122 receives input data 400 (as shown in FIG. 4) over the communications network 116 that is generated by the one or more clinical care environment systems 100. The detection system 122 analyzes the input data 400 and generates system outputs 204 (as shown in FIG. 2) that are transmitted to the one or more communications devices 102 via the communications network 116. The system outputs 204 may include locations of individuals within the clinical care environment 10, one or more alerts, and one or more recommendations, which are described and illustrated in further detail with respect to FIG. 5.

In certain examples, a caregiver C can manually request an alert and/or recommendation from the detection system 122 via the one or more communications devices 102. The one or more communications devices 102 transmits the request to the detection system 122 via the communications network 116. The detection system 122 can process the request, generate an alert and/or a recommendation or update a previous alert and/or recommendation, and transmit the alert and/or recommendation to the communications device 102 via the communications network 116.

In another example, the detection system 122 can proactively generate the one or more system outputs 204 and transmit the system outputs 204 to a non-violent individual. In certain examples, the system output 204 automatically generates the system outputs 204 when the detection system 122 identifies at least one individual exhibiting violent behavior (also referred to as a violent individual V) and detects a location of the at least one individual exhibiting violent behavior (as illustrated and described in further detail with respect to FIG. 3). In certain examples, the at least one individual exhibiting violent behavior is automatically identified using a plurality of identification factors as illustrated and described in further detail with respect to FIG. 9. In certain examples, the detection system 122 may automatically update the one or more system outputs 204 in real time based on a continuous monitoring of individuals within the clinical care environment 10, which is described and illustrated in further detail with respect to FIGS. 10-11.

In other examples, a patient P can manually request an alert and/or recommendation from the detection system 122 via a clinical care environment system 100 (e.g., the caregiver call system 120) and receive the one or more system outputs 204 that are communicated either visually or auditorily (e.g., through a monitor on a spot monitor or through speakers positioned on a patient bed 101 such as a patient pillow speaker 103). In some examples, the one or more system outputs 204 can be transmitted to the patient P automatically when an individual exhibiting violent behavior is identified.

Advantages of the detection system 122 for the patient P and caregiver C can include improving the safety of healthcare facilities and the overall efficiency of emergency protocols within a clinical care environment 10 by quickly and effectively identifying one or more individuals who are exhibiting violent behavior. Furthermore, the detection system 122 provides efficient alerts and/or recommendations that provide critical information and help individuals avoid danger. Further yet, the detection system 122 manages violent situations by contacting emergency services to share information relating to the clinical care environment 10 and the individuals, tracking the movement of individuals within the clinical care environment 10, and providing updates to the system outputs 204 based on the locations of the individuals. Still further yet, the detection system 122 can generate recommendations for treating one or more patients P and/or caregivers C for injuries or trauma that are sustained during a violent event.

As shown in FIG. 1, one or more clinical care environment systems 100 collect input data 400 (see FIG. 4). For example, the ADT system 108 is connected to the communications network 116. The ADT system 108 tracks patients from their moment of arrival at the clinical care environment 10 until their departure and can store relevant patient information such as medical record numbers, names, and contact information. Data acquired from the ADT system 108 can be used to determine information that is useful for tracking individuals during a violent event, determining whether any patients P are missing after the violent event has ended, and providing useful information to emergency service providers to aid in the recovery of the patient or the apprehension of the violent individual.

As further shown in the example provided in FIG. 1, the caregivers C each wear or otherwise carry a tag 104 that is detectable by antennas 114 (also referred to as RTLS readers) positioned throughout the clinical care environment 10. The antennas 114 are fixed reference points that receive wireless signals from the tags 104. The antennas 114 communicate the wireless signals from the tags 104 to the RTLS 110 via the communications network 116. The RTLS 110 uses the data acquired from the antennas 114 to monitor and track the location of the tags 104 (and of the caregivers C) inside the clinical care environment 10. In some examples, the antennas 114 and the tags 104 are considered to be part of the RTLS 110.

Alternatively, the location of the caregivers C can be monitored by tracking the movement of the communications devices 102. In examples where the communications devices 102 are portable computing devices such as smartphones or table computers carried by the caregiver C, the location of the communications devices 102 can be tracked by various tracking techniques including multilateration of signals between cell towers of a telecommunications network and the communications devices 102, or by using geo-spatial positioning techniques by satellite navigation systems such as the Global Positioning System (GPS).

As shown in the example provided in FIG. 1, the EMR system 124, also known as electronic health records (EHR) system, is connected to the communications network 116. The EMR system 124 stores the medical history of the patient P. In certain examples, the EMR system 124 generates EMR data 402 (see FIG. 4) that includes information about the patient's P diagnoses (including a current primary diagnosis), past or current medicines that the patient P is taking, physiological variable measurements of the patient P, clinical interventions provided to the patient P, allergies, immunizations, and treatment plans. The EMR data 402 is illustrated and described in further detail with respect to FIG. 4.

As further shown in the example provided in FIG. 1, the caregiver call system 120 is connected to the communications network 116. The caregiver call system 120 receives requests from the patient P, and can generate and send alerts to the one or more caregivers C to respond to the requests from the patient P. In certain examples, the alert can be routed via the communications network 116 to a communications device 102 used by the caregiver C during their shift. In certain examples, the alert can include information retrieved from the EMR system 124 or from an alarm communication system.

In certain examples, the caregiver call system 120 includes one or more caregiver call lights (also known as corridor lights or dome lights) outside of a patient room that indicate when a patient P is requesting help from a caregiver C. The caregiver call lights may also be used to discreetly provide a visual indication to a caregiver C, without the patient P observing the visual indication from within the patient room, that a violent individual has been detected within the clinical care environment 10. This prompts the caregiver C to review communications from the detection system 122 via their communications device 102 without causing panic among patients within the clinical care environment 10. Furthermore, the caregiver call lights may be used to visually indicate an escape route to the closest exit within the clinical care environment 10 to lead the patients P and caregivers C to safety during a violent event. The functionality of the caregiver call lights are illustrated and described in further detail with respect to FIGS. 5-6.

As further shown in the example provided in FIG. 1, the audio system 126 is connected to the communications network 116. The audio system 126 includes a plurality of speakers positioned throughout the clinical care environment 10 that allow auditory communication between caregivers C, patients P, and the detection system 122. In certain examples, the speakers may be included within patient rooms (e.g., on a patient bed 101 such as a patient pillow speaker 103, or a patient monitoring device such as a spot monitor) or within common spaces within the clinical care environment 10 (e.g., hallways, communal spaces, dining areas, and the like). Furthermore, the audio system 126 auditorily provides information pertaining to system outputs 204. In certain examples, the information conveyed by the audio system 126 to a caregiver C or patient P may include a simple alert (such as an alarm) or it may convey a more complex message through voice communication.

Figure 9:
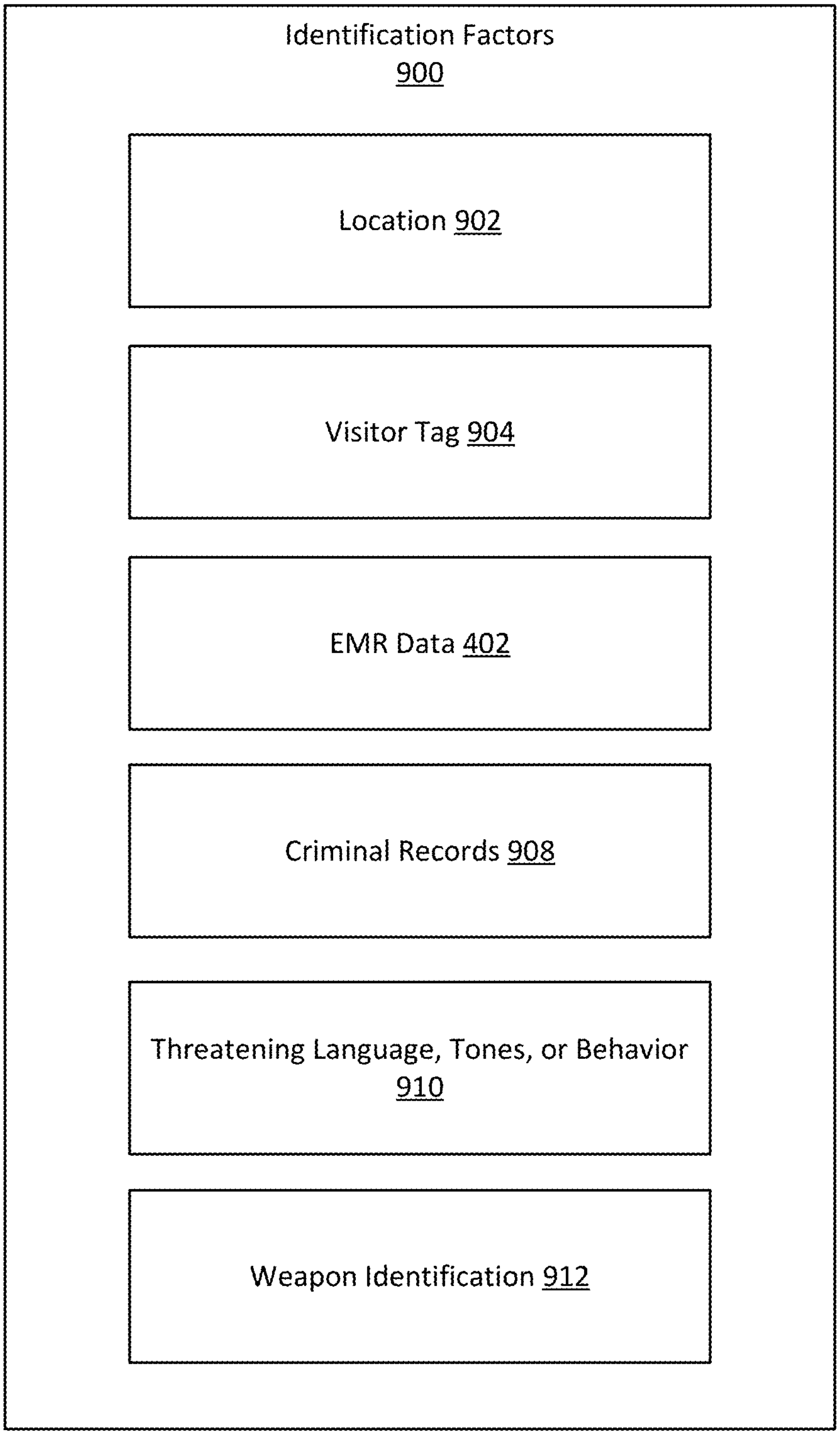
FIG. 9 schematically illustrates examples of violent individual identification factors that can be considered by the detection system of FIG. 1 when identifying a violent individual.

Furthermore, the audio system 126 may be used to record audio that is transmitted to the detection system 122 to be used to identify signs of violence within a clinical care environment 10, which is illustrated and described in further detail with respect to FIG. 9. In certain examples, the audio system 126 may record signs of violence that include screaming, threatening language, gun shots, or sudden loud noises.

As further shown in the example provided in FIG. 1, the camera system 128 is connected to the communications network 116. The camera system includes a plurality of cameras (e.g., video cameras, surveillance cameras, and the like) positioned throughout the clinical care environment 10 that monitor movements of individuals. The camera system 128 may include cameras positioned within patient rooms or in common spaces. The camera system 128 may be used to record video that is transmitted to the detection system 122 to be used to identify signs of violence within a clinical care environment 10, which is illustrated and described in further detail with respect to FIG. 9. In certain examples, the audio system 126 may record signs of violence that include threatening behavior, sudden movements, a visual identification of a weapon, or other signs.

FIG. 2 schematically illustrates an example of the detection system 122. The detection system 122 is connected to the communications network 116 via a network interface 206 to facilitate a transfer of data to and from the detection system 122. In certain examples, the network interface 206 is a physical network interface that is a hardware component installed within a computer or other device. In certain examples, the network interface 206 is a virtual network interface used in virtualized environments that allows a virtualized system to communicate with a physical network.

The detection system 122 receives the input data 400 (see FIG. 4) from the one or more of the clinical care environment systems 100 over the communications network 116. Examples the clinical care environment systems 100 are illustrated and described in further detail above with respect to FIG. 1. The clinical care environment systems 100 store the input data 400, and system outputs 204 that are produced by the detection system 122 (through a process described below) within a system memory 202.

The detection system 122 receives the input data 400 via the communications network 116. A system processor 210 processes the input data 400. In certain examples, the detection system 122 continuously receives the input data 400 from the one or more of the clinical care environment systems 100, and continuously updates the system outputs 204 over time. In certain examples, the detection system 122 provides an explanation for why an update to the system outputs 204 occurred.

The system processor 210 receives and executes instructions from the system memory 202, and specifically a violence detection program 208, to process the input data 400 received over the communications network 116. In some examples, this includes utilizing one or more artificial intelligence models to process the input data 400 and generate the system outputs 204. For instance, a machine learning algorithm can be trained using input data 400 from a large number of patients P. Examples of applications using the violence detection program 208 are illustrated and described in further detail with respect to FIGS. 5-11.

The system memory 202 includes one or more memories configured to store the violence detection program 208. In certain examples, the system memory 202 stores the input data 400 received via the communications network 116. In this example, the system memory 202 stores at least one set of input data 400 that includes any combination of the data illustrated and described in further detail with respect to FIG. 4.

In certain examples, the system memory 202 stores the system outputs 204. In this example, the system memory 202 stores at least some of the system outputs 204 illustrated and described in further detail with respect to FIG. 5.

The system memory 202 can be of various types, including volatile and nonvolatile, removable, and non-removable, and/or persistent media. In some examples, the system memory 202 is an erasable programmable read only memory (EPROM) or flash memory.

The communications device 102 transmits one or more requests 212 to the detection system 122 and receives system outputs 204 via the communications network 116. The one or more requests 212 may be manually generated by a caregiver C such as when the caregiver C requests a recommendation from the detection system 122 via the communications device 102. The communications device 102 stores and displays the system outputs 204 for a caregiver C to review. Examples of the system outputs 204 that can be generated on the communications devices 102 are illustrated and described in further detail with respect to FIGS. 8 and 9.

Figure 3:
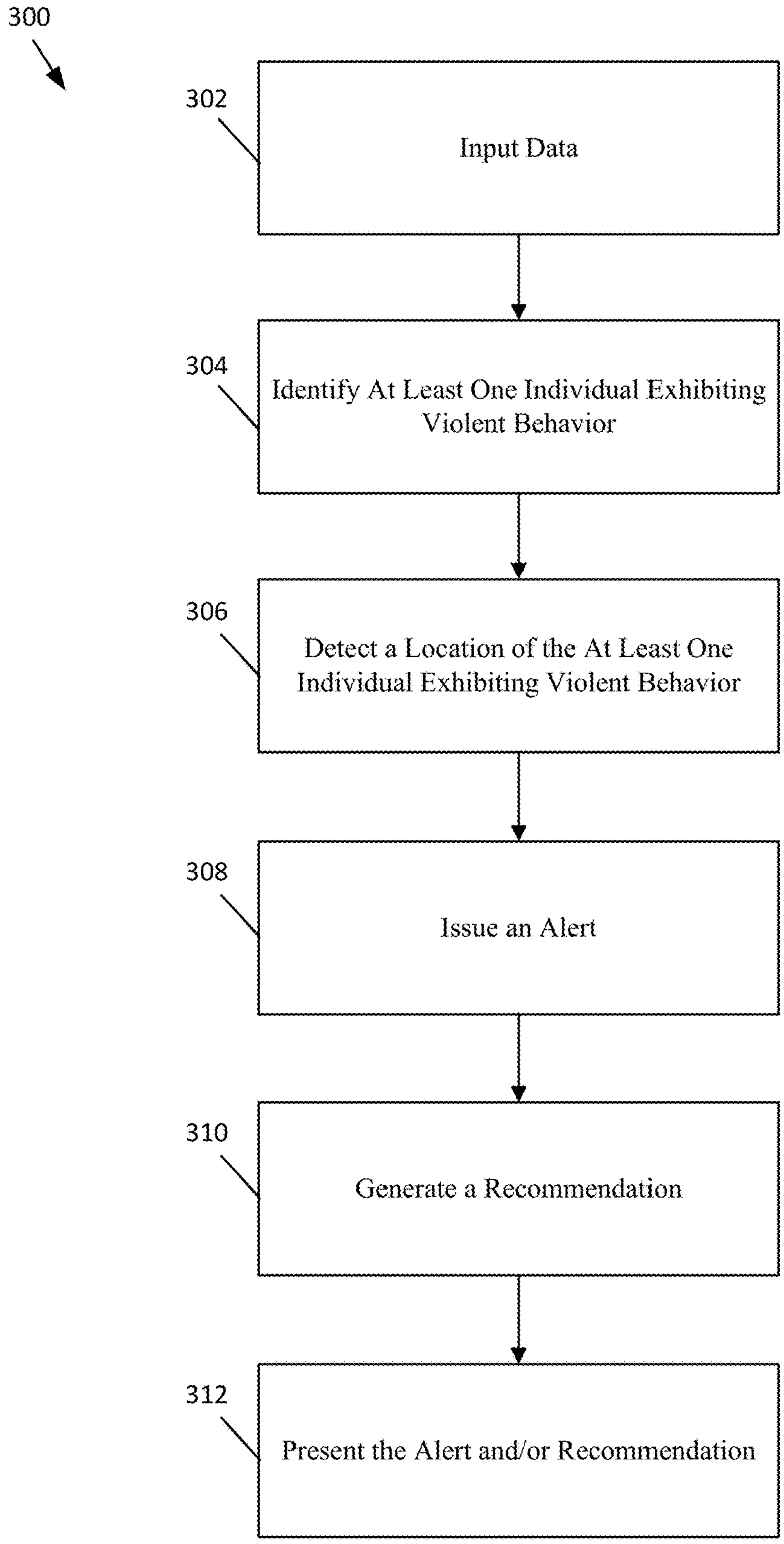
FIG. 3 schematically illustrates an example of a method of identifying a violent individual, detecting the violent individual's location, and generating an alert based on the violent individual's location.

FIG. 3 schematically illustrates an example of a method 300 of mitigating danger or harm during a violent event. The method 300 can be performed by the detection system 122. The method 300 includes a step 302 of receiving the input data 400. As described above, the input data 400 is generated by the one or more clinical care environment systems 100. The input data 400 is received from the one or more clinical care environment systems 100 via the communications network 116 as described and illustrated in further detail with above in FIG. 2.

The method 300 includes a step 304 of identifying at least one individual exhibiting violent behavior. Step 304 is performed by analyzing the input data 400 received in step 302. The individual exhibiting the violent behavior is identified based on one or more identification factors 900 (see FIG. 9) that are identified from the input data 400. The one or more identification factors 900 are illustrated and described in further detail with respect to FIG. 9.

In certain examples, the detection system 122 analyzes the input data 400, identifies one or more identification factors 900, and generates a confidence rating that an individual is exhibiting violent behavior. In certain examples, the confidence rating is reviewed to confirm an individual is exhibiting violent behavior when the confidence rating is below a threshold rating. Furthermore, step 304 may include identifying whether the violent behavior is intentional (i.e., whether an individual intends to cause harm to others or if an individual is acting in an uncontrollable fashion due to a medical event). If the violent behavior appears to be unintentional, then the confidence rating may be reduced, the detection system 122 may request further validation, or the detection system 122 may elect not to issue an alert or recommendation.

The method 300 includes a step 306 of detecting a location of the at least one individual exhibiting the violent behavior. The detection system 122 may detect the location of the individual exhibiting violent behavior by analyzing data collected by the one or more clinical care environment systems 100 (e.g., analyzing data collected by the audio system 126 or camera system 128 to monitor the movements of the individual exhibiting the violent behavior).

In certain examples, the individual exhibiting the violent behavior may be tracked using the RTLS 110. In some examples, one or more wireless tags, such as radio-frequency identification (RFID) tags, can be coupled to the at least one individual who is exhibiting the violent behavior. In some examples, a tagging device 624 (see FIG. 6) can be controlled to fire a projectile at the individual, the projectile containing the one or more RFID tags for tagging the individual. In some further examples, the tagging device 624 can be controlled to spray an ink that is detectable by the camera system 128 or the RTLS 110 for tracking the location of the individual exhibiting the violent behavior within the clinical care environment 10.

In a non-limiting example, the tagging device 624 may be positioned at locations within the clinical care environment 10 where the individual exhibiting the violent behavior is likely to pass through, such as doorways in hallways, common areas, or patient rooms. The tagging device 624 may be activated by the detection system 122 to fire the projectile at the individual exhibiting the violent behavior based on the monitored location of the individual exhibiting the violent behavior and the location of the tagging device 624. Furthermore, the tagging device 624 may include a mechanism for aiming the tagging device 624. The tagging device 624 is illustrated and described in further detail with respect to FIG. 6.

The method 300 includes a step 308 of issuing an alert. As described above with reference to FIGS. 1-2, the alert can be issued to a caregiver C or a patient P via a communications device 102 or other devices located within the patient environment 12, such as the audio system 126, a patient pillow speaker 103 on the patient bed 101, the spot monitor 105, and/or a display device such as a television. Examples of alerts are illustrated and described in further detail with respect to FIGS. 5 and 7.

The method 300 includes a step 310 of generating a recommendation. As described above, the recommendation can be provided to a caregiver C or a patient P via a communications device 102 or other devices located within the clinical care environment 10, such as the audio system 126, the patient bed 101, and the like. Examples of recommendations are illustrated and described in further detail with respect to FIGS. 5-6, 8, and 9-11.

The method 300 includes a step 312 of presenting the alert and/or recommendation. As illustrated and described above, the alert and/or recommendation can be presented to a caregiver C or a patient P via a communications device 102 or other devices located within the clinical care environment 10 such as the audio system 126, a patient pillow speaker 103 on the patient bed 101, the spot monitor 105, and/or a display device such as a television.

FIG. 4 schematically illustrates examples of input data 400 that can be generated by the one or more clinical care environment systems 100. As described above, the clinical care environment systems 100 can include the ADT system 108, the RTLS 110, the caregiver call system 120, the EMR system 124, the audio system 126, and the camera system 128. The input data 400 can include one or more of EMR data 402, ADT system data 404, RTLS data 406, caregiver call system data 408, audio system data 410, and camera system data 412. The detection system 122 analyzes the one or more of the EMR data 402, ADT system data 404, RTLS data 406, caregiver call system data 408, audio system data 410, and camera system data 412, including any combinations thereof, to generate system outputs 204, which are described and illustrated in further detail with respect to FIGS. 5-8.

As described above, the EMR data 402 includes information about a patient P's medical history, including diagnoses, past or current medicines that the patient P is taking, clinical interventions provided to the patient P, recorded vital sign measurements, and other physiological variable measurements, allergies, immunizations, and treatment plans. In certain examples, the caregiver C can enter the EMR data 402 into the EMR system 124 using a communications device 102. In certain examples, the EMR data 402 is utilized to generate system outputs 204 by considering a patient's condition, any physical limitations that would hinder the patient's ability to exit the clinical care environment 10 during a violent event, or other limitations that would affect the patient's ability to understand instructions.

The ADT system data 404 is generated by the ADT system 108. As described above, the ADT system 108 tracks patients from their moment of arrival at the clinical care environment 10 until their departure, and can store relevant patient information such as medical record numbers, names, and contact information. In certain examples, the ADT system data 404 can be utilized to generate system outputs 204 by considering the number of patients P that are admitted to the clinical care environment 10, demographic information pertaining to each patient P, and a list of patients P to be accounted for after the violent event has ended.

The RTLS data 406 is generated by the RTLS 110. As described and illustrated above with respect to FIG. 1, the RTLS 110 uses the data acquired from the antennas 114 to monitor and track the location of the tags 104 (and the caregivers C) inside the clinical care environment 10. In certain examples, the detection system 122 utilizes the RTLS data 406 to generate the system outputs 204 by monitoring the locations of caregivers C, or any other individuals that are equipped with a tag 104, in real time. In certain examples, the locations of individuals that are tracked with the RTLS 110 is monitored in real-time to update the system outputs 204 and provide one or more updated outputs to a caregiver C or patient P.

The caregiver call system data 408 is generated by the caregiver call system 120. As described and illustrated above with respect to FIG. 1, the caregiver call system 120 receives requests from a patient P and sends an alert to a caregiver C to respond to the requested received from the patient P. In certain examples, the detection system 122 can analyze the caregiver call system data 408 to locate, and communicate with patients P that require assistance during a violent event. Furthermore, the detection system 122 can generate alerts that are displayed by a caregiver call light and update the alerts in real time while a violent event is in progress.

The audio system data 410 is generated by the audio system 126. As described above, the audio system data 410 can be utilized by the detection system 122 to identify an individual that is exhibiting violent behavior. In further examples, the audio system data 410 can be utilized by the detection system 122 to provide a system output 204.

The camera system data 412 is generated by the camera system 128. As described above with reference to FIG. 1, in certain examples, the camera system data 412 can be utilized by the detection system 122 to identify an individual that is exhibiting violent behavior.

Figure 5:
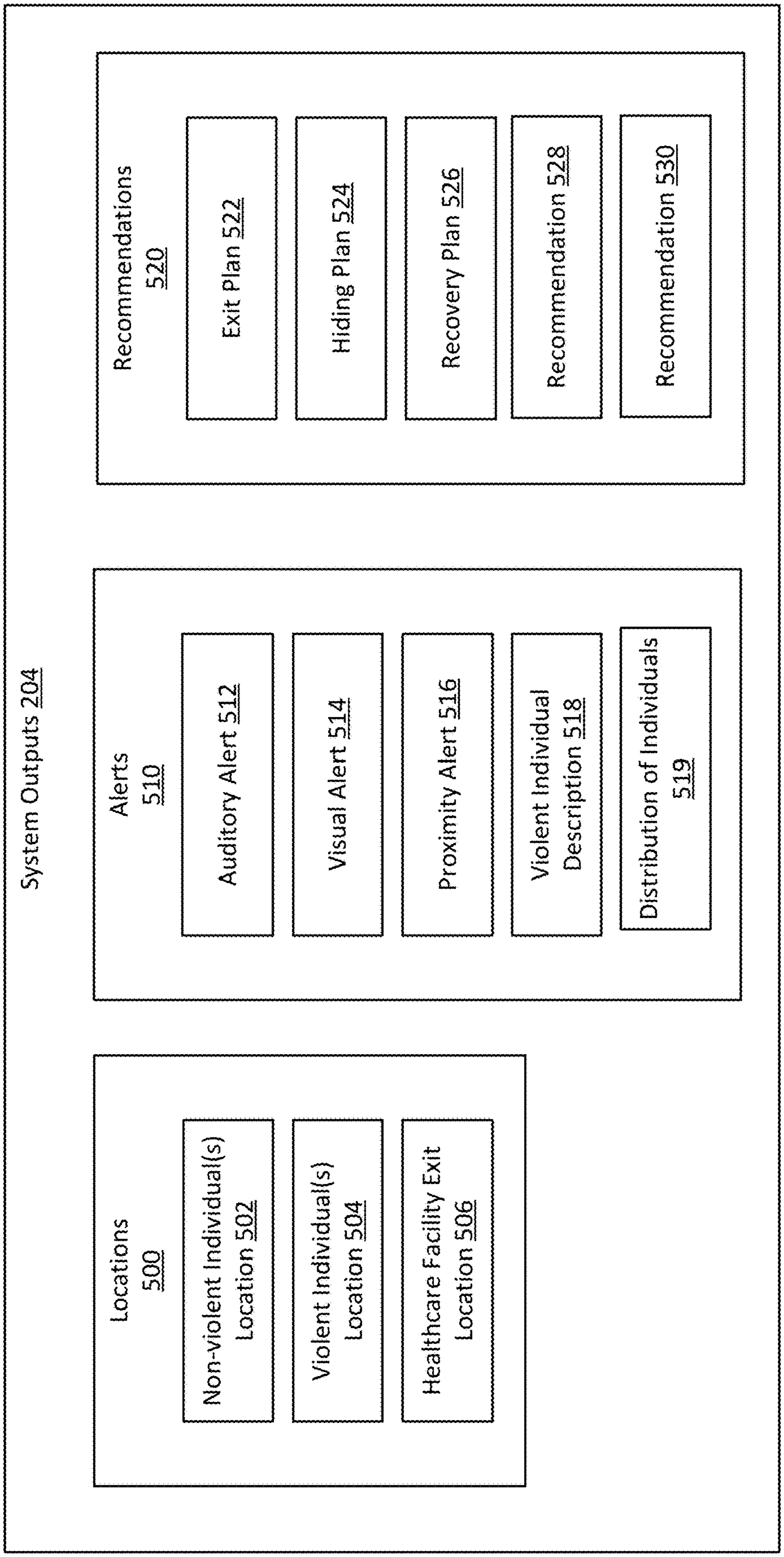
FIG. 5 schematically illustrates examples of outputs that can be generated by the detection system of FIG. 1.

FIG. 5 schematically illustrates examples of system outputs 204 that can be generated by the detection system 122. In certain examples, the system outputs 204 include locations 500, alerts 510, and recommendations 520, which are each described in further detail below.

The locations are calculated by the detection system 122. The locations 500 include a non-violent individual's location 502, a violent individual's location 504, and a clinical care environment exit location 506. The detection system can calculate the locations 500 by analyzing the input data 400 that includes a location of each individual within the clinical care environment 10. The location of each individual can be compared to one or more clinical care environment exit locations 506, which are included in a floor plan for the clinical care environment 10. Examples of a process for classifying the individuals as being violent or non-violent are illustrated and described in further detail with respect to FIGS. 3 and 9. In certain examples, the non-violent individual(s) location 502, the violent individual(s) location 504, and the clinical care environment exit locations 506 are used to generate an exit plan 522 as part of a recommendation 520, which is described below and further illustrated in FIG. 6.

The alerts 510 include an auditory alert 512, a visual alert 514, a proximity alert 516, and a violent individual description 518. In certain examples, the alerts 510 are accompanied by one or more recommendations 520. The alerts 510 may be issued simultaneously while communicating a request to law enforcement to neutralize a violent individual.

One or more auditory alerts 512 can be generated by the detection system 122 and communicated via the audio system 126, the caregiver call system 120, a communications device 102, or through a patient device (e.g., the patient pillow speaker 103 positioned on the patient bed 101) to indicate the presence of an individual exhibiting violent behavior. In certain examples, information conveyed within an audio alert to a caregiver C or patient P may include a simple alarm or it may convey a more complex message through voice communication (e.g., a caregiver may speak over a communications system, a pre-recorded voice may communicate the alert, or the detection system 122 may automatically generate an auditory alert that includes spoken language). An auditory alert 512 may be transmitted discreetly to a caregiver C via a communications device 102 without communicating the auditory alert 512 to patients P to prevent panic within the clinical care environment 10.

In certain examples it may be undesirable to obtain an auditory alert 512 to avoid being detected by a violent individual. In these scenarios, the detection system is configured to automatically silence any communications device 102 within a threshold distance of the individual exhibiting violent behavior.

One or more visual alerts 514 can be generated by the detection system 122. In certain examples, the visual alerts 514 include text and/or drawings that describe the nature of the alert. A visual alert 514 may be transmitted discreetly to a caregiver C via a communications device 102 without communicating the visual alert 514 to patients P to prevent panic within the clinical care environment 10. Furthermore, the visual alert 514 may be displayed on a nurse call light positioned outside of a patient room to alert caregivers C of a violent event that is taking place. In certain examples, the visual alert 514 when implemented on a nurse call light can include a plurality of colors that uniquely identify different types of events to efficiently inform the caregivers C of a type of violent event that is taking place.

One or more proximity alerts 516 can be generated by the detection system 122 and communicated to patients P and caregivers C based on a distance between the non-violent individual and the patient P or the caregiver C. The distance between the caregiver C or the patient P and the violent individual is calculated by determining the non-violent individual's location 502 and the violent individual's location 504 as described above. In certain examples, the proximity alert 516 is issued to the caregiver C or the patient P when the distance between the caregiver C or the patient P and the violent individual is below a threshold value.

The alerts 510 can include a violent individual description 518. The violent individual description 518 provides identifiable characteristics of the violent individual to the recipient of the alert (i.e., a caregiver C) to help the recipient distinguish between the violent individual(s) and other non-violent individuals. This is desirable to help the non-violent individuals avoid contact with the violent individual. In certain examples, the violent individual description 518 is communicated to law enforcement services in conjunction with issuing the alert 510.

In certain examples, the alert 510 includes a distribution of individuals 519 across a visual map of the clinical care environment, wherein the visual map includes a visual indicator of a distances between a non-violent individual and the violent individual(s) or the non-violent individual and other non-violent individuals.

The recommendations 520 include one or more of an exit plan 522, a hiding plan 524, a recovery plan 526, a recommendation 528 to manipulate one or more door locks within the clinical care environment 10, or a recommendation 530 to manipulate one or more patient devices within the clinical care environment.

The exit plan 522 includes a floor map of the clinical care environment with an exit path. In certain examples the exit path is generated as a minimum distance between a current location of a user carrying or using the communications device 102 and an exit of the clinical care environment 10. Furthermore, the detection system 122 may generate the exit path by further considering the distance between other individuals not exhibiting the violent behavior and the exit, which is described and illustrated in further detail with respect to FIGS. 6 and 10. Further yet, the detection system 122 may consider the distance between the individual who is exhibiting the violent behavior and the exit when calculating the exit path, which is described and illustrated in further detail with respect to FIGS. 6 and 11.

The hiding plan 524 includes a floor map of the clinical care environment 10 with a path to a safe room 606 (see FIG. 6) that is closest to a current location of the individual. The safe room 606 includes a door that is accessible to caregivers C and patients P that may be locked manually, or automatically by the detection system 122, if an individual exhibiting the violent behavior is located near the safe room. The safe room 606 may include certain characteristics such as limited visibility looking into the room, a powerful locking device on an entry into the safe room 606, limited entry points into the safe rooms 606, sufficient supplies (e.g., food, water, proper ventilation, etc.) in case the violent event lasts a prolonged period of time, and speakers equipped to the audio system 126 to communicate with other individuals outside of the safe room 606. The hiding plan 524 and an example of safe rooms 606 are illustrated and described in further detail with respect to FIG. 6.

The recovery plan 526 includes one or more recommendations to aid in the physical and mental recovery of a patient P or caregiver C after the violent event has ended. The recovery plan helps caregivers C treat patients P or other caregivers C for any injuries sustained during the violent event. In certain examples, the detection system 122 generates a recovery plan that considers data collected during the violent event, which data can be collected from the one or more clinical care environment systems 100.

The recommendation 528 to manipulate door locks includes locking one or more doors within the clinical care environment 10 to confine the individual who is exhibiting the violent behavior. In certain examples, the recommendation 528 to manipulate door locks can be implemented automatically without input from the patient P or the caregiver C. It is desirable to confine the individual who is exhibiting the violent behavior to a certain area within the clinical care environment 10 to protect individuals outside of the confined area while helping emergency services (e.g., law enforcement services) locate and apprehend the violent individual.

The recommendation 530 to manipulate patient devices includes adjusting a patient device to help a patient P or caregiver C execute one or more recommendations 520. In certain examples, the recommendation 530 to manipulate patient devices includes turning a patient bed 101 to help the patient P move out of the patient bed 101. In certain examples, the detection system 122 can automatically perform the recommendation 530 to manipulate a patient device.

Figure 6:
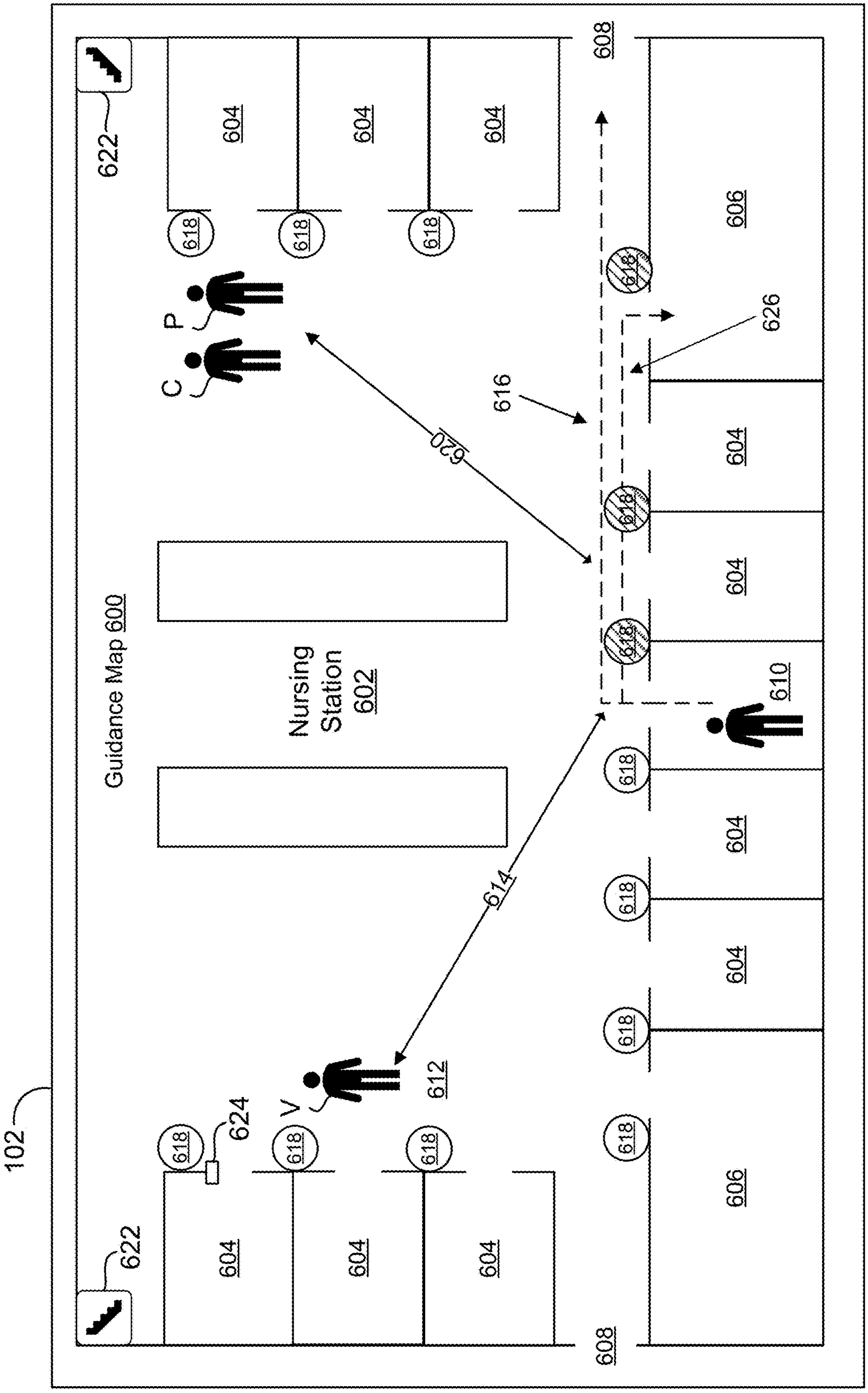
FIG. 6 illustrates an example of a guidance map that can be displayed on a communications device by the detection system of FIG. 1.

FIG. 6 illustrates an example of a guidance map 600. The guidance map 600 can be displayed on a communications device 102 carried by a caregiver C. Alternatively, or additionally, the guidance map 600 can be displayed on a display of a medical device within the clinical care environment 10 such as the patient bed 101 and/or the spot monitor 105. The guidance map 600 displays an example of the exit plan 522 that includes an exit path 616 from a current location 610 to an exit 608. Furthermore, the guidance map 600 displays an example of a hiding plan 524 that includes a safe room path 626 to a safe room 606. The hiding plan 524 and the exit plan 522 are generated by the detection system 122. In certain examples, the violence detection program 208 generates the hiding plan 524 and the exit plan 522.

The exit plan 522 includes a plurality of rooms 604, safe rooms 606, exits 608, a nursing station 602, and a current location 610 of a patient P or a caregiver C that received the exit plan 522. Furthermore, the floor plan includes nurse call lights 618 outside of each room along an exit path 616 to visually indicate the exit path to a user of the communications device 102, and other caregivers C and patients P in the clinical care environment 10 (as shown in FIG. 6 with nurse call lights 618 that are illustrated as shaded to visually indicate the exit path 616). Further yet, the floor plan includes stair wells 622 that may be manually locked by a caregiver C or patient P, or automatically locked by the detection system 122, to confine the violent individual V to a specific floor. Still further yet, one or more rooms may include the tagging device 624 positioned at an entry of one or more of the plurality of rooms 604.

The exit plan 522 includes the exit path 616 that directs the patient P or the caregiver C to an exit 608 that is closest to their current location 610. In certain examples, the exit path 616 considers a first distance 614 between the current location 610 and a violent individual 612. In certain examples, the exit path 616 considers a second distance 620 between the current location 610 and one or more other caregivers C or patients P. Furthermore, the exit path 616 may consider both the first distance 614 and the second distance 620 when calculating the exit path 616. When calculating the exit path 616, the detection system 122 may compare the first distance 614 or the second distance 620 to a threshold value and recalculate the exit path 616 if at least one of the first distance 614 or the second distance 620 is below a threshold value (which is illustrated and described in further detail with respect to FIGS. 10-11).

In certain examples, the exit plan 522 may also include a safe room path 626. Providing a safe room path 626 is desirable to allow a caregiver C or patient P to enter a safe room 606 in case an exit 608 is blocked or if the caregiver C or patient P is otherwise unable to reach the exit 608. In certain examples, only one of the exit path 616 or the safe room path 626 is displayed in the exit plan 522 based on the physical limitations of a patient P or caregiver C such as when they are enabled to escape due to limited mobility.

Figure 7:
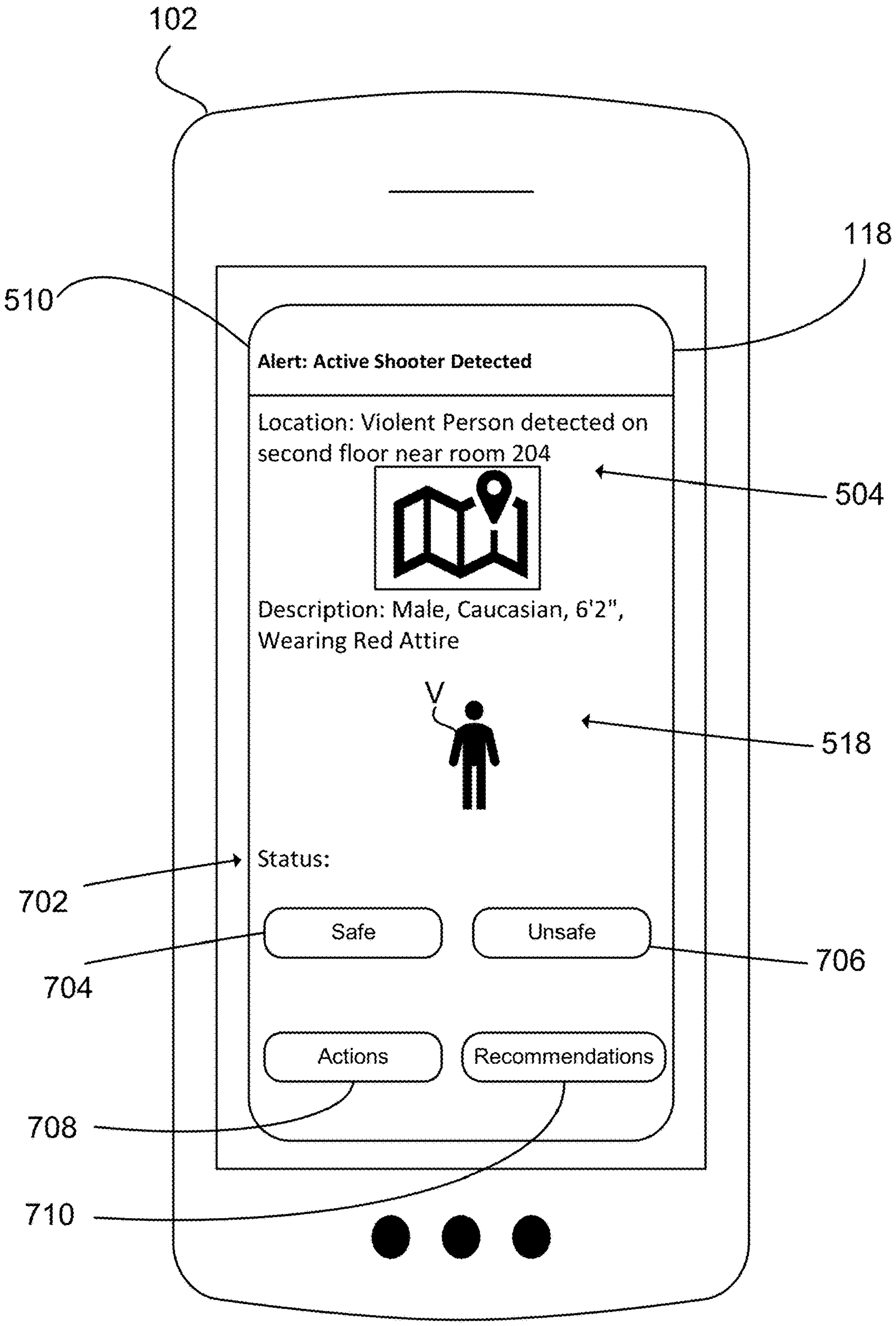
FIG. 7 illustrates an example of a communications device displaying an active shooter alert that can be generated by the detection system of FIG. 1.

FIG. 7 illustrates an example of a communications device 102 displaying an alert 510 relating to an active shooter that can be generated by the detection system 122. In this example, the alert 510 is displayed on a display 118 of the communications device 102. The display 118 can include a touchscreen that displays outputs and receives tactile inputs from the caregiver C. Alternatively, or additionally, the alert 510 can be displayed on a display of a medical device within the clinical care environment 10 such as the patient bed 101 and/or the spot monitor 105.

The alert 510 includes the violent individual's location 504 that can be updated in real time. In certain examples, the violent individual's location 504 is displayed on a floor map of the clinical care environment 10, such as shown in FIG. 6. Furthermore, the alert 510 includes the violent individual description 518 that helps caregivers C and patients P identify the violent individual. Further yet, the alert 510 includes a request to receive a status 702 of the user (e.g., a patient P or caregiver C). The status request includes a safe icon 704 on the display 118 that, when selected by the user, communicates to the detection system 122 that the user is in a safe location. Furthermore, the status request includes an unsafe icon 706 on the display 118 that indicates the user is not in a safe location. Further yet, the alert 510 includes an actions icon 708 on the display 118 for requesting the detection system 122 to initiate one or more actions (e.g., contact emergency services) and a recommendations icon 710 on the display 118 for viewing the recommendations 520 from the detection system 122, such as the exit plan 522 shown in FIG. 6.

Figure 8:
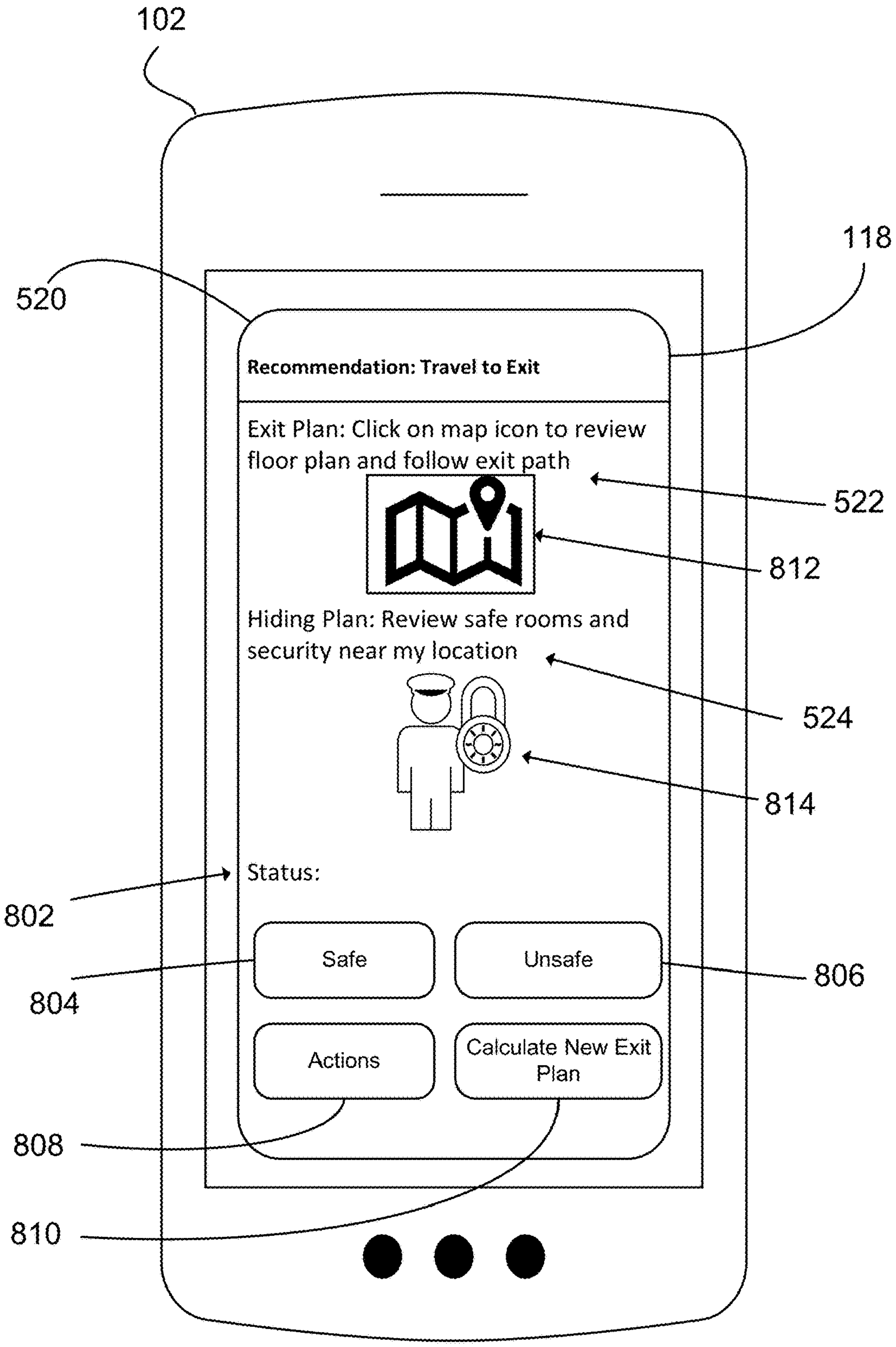
FIG. 8 illustrates an example of a communications device displaying an active shooter recommendation that can be generated by the detection system of FIG. 1.

FIG. 8 illustrates another example of a communications device 102 displaying a recommendation 520 that can be generated by the detection system 122. In this example, the recommendation 520 is displayed on the display 118 of the communications device 102. Alternatively, or additionally, the recommendation 520 can be displayed on a display of a medical device such as the patient bed 101 and/or the spot monitor 105.

The recommendation 520 includes a recommendation for the user of the communications device 102 to travel to the nearest exit. As illustrated and described above with reference to FIG. 6, a recommendation to travel to an exit or a safe room can be made based on several factors, including the user's physical and mental ability to travel to the exit and the user's proximity to the violent individual or other non-violent individuals.

The recommendation 520 includes an exit plan 522 and a hiding plan 524 as illustrated and described in further detail with respect to FIGS. 5 and 6. In certain examples, the exit plan 522 and the hiding plan 524 include icons 812, 814 that allow the user to view the exit path 616 or the safe room path 626. In certain examples, a user may view the exit plan 522 and/or the hiding plan 524 by selecting a single icon displayed on the display 118 of the communications device 102. As shown in FIG. 8, the user may select the icons 812, 814 to view an exit path 616 and/or a safe room path 626, examples which are shown in FIG. 6.

The recommendation 520 can also include a request to receive a status 802 of the user. For example, a safe icon 804 is included on the display 118 that, when selected by the user, communicates to the detection system 122 that the user is in a safe location. Also, an unsafe icon 806 can be included on the display 118 that, when selected by the user, communicates to the detection system 122 that the user is not in a safe location.

In certain examples, after the user indicates their status 802, the detection system 122 may generate an all-clear alert when the violent individual no longer poses a threat to a non-violent individual. Furthermore, the detection system 122 may transmit the all-clear alert to the non-violent individuals using a communications device 102, patient device, or other means.

Further yet, the recommendation 520 includes an actions icon 808 on the display that, when selected by the user, displays a plurality of requests that can be made by the user. In certain examples, the actions icon 808 allows the user to request other recommendations and/or implement one or more of the recommendations that were provided. For example, the user may request a recovery plan 526, the user may request a recommendation 528 to manipulate door locks, or the user may request a recommendation 530 to manipulate one or more patient devices. Alternatively, the user may request the detection system 122 automatically implement the recommendation 528 to manipulate door locks or the recommendation 530 to manipulate one or more patient devices. Additionally, the recommendation 520 includes a calculate new exit plan icon 810 that when selected causes the detection system 122 to generate a new or an alternative exit path for the user to escape the clinical care environment 10 to reach safety.

FIG. 9 schematically illustrates examples of identification factors 900 that are considered by the detection system 122 to identify a violent individual. The identification factors 900 include a location 902 of an individual within the clinical care environment 10. For example, when the individual is located near a point where loud noises or sudden movements are originating from, then the individual might be more likely to be exhibiting violent behavior. Loud noises can be recorded by the audio system 126 and identified by the detection system 122. Sudden movements can be recorded by the camera system 128 and identified by the detection system. Furthermore, sudden movements may be identified by information received from a tag. In certain examples, the tagging device 624 can be controlled by the detection system 122 to fire a projectile containing a wireless tag or ink that is recognizable by the RTLS 110 or camera system 128, as illustrated and described above in further detail with respect to FIGS. 3 and 6.

Once the wireless tag or ink is coupled to the at least one violent individual, the RTLS 110 is configured to establish a first connection between the detection system 122 and at least one reader, establish a second connection between the at least one reader and the wireless tag, associate the wireless tag with the at least one individual, and monitor the location of the at least one individual based on signals from the at least one reader measuring a distance between the wireless tag and the at least one reader.

The identification factors 900 include a visitor tag 904. In some examples, the visitor tag 904 includes the wireless tag that can be tracked by the RTLS 110. In some alternative examples, the visitor tag 904 includes a visual indicator that is associated with a perceived level of risk for a visitor that is attending the clinical care environment 10. For example, the detection system 122 may determine, based on the input data 400, that an individual has a propensity for violence. The detection system 122 may then recommend that the individual receive a visitor tag that corresponds to a risk associated with that individual. In certain examples, the risk associated with the individual is measured on a quantifiable scale (e.g., a scale from 1-10). In certain examples, the visual indicator includes a color, a machine-readable code (e.g., a quick response (QR) code or bar code), or other type of visual indicator that is uniquely associated with the risk associated with the individual. The visitor tag 904 can be viewed by the camera system 128 and the visual indicator can be identified by the detection system 122. The detection system 122 monitors and tracks the location of the individual wearing the visitor tag 904 that is associated with an elevated risk of violence. An example of the visitor tag 904 is illustrated and described in further detail with respect to FIG. 11.

The identification factors 900 can further include the EMR data 402. The detection system 122 can assign a perceived level of risk to an individual based on past medical events that are documented in the EMR data 402. For example, a patient P who has a documented medical condition that affects their ability to control anger combined with past documentation of violent outbursts may be more likely to exhibit violent behavior. EMR data 402 may be analyzed by the detection system 122.

In certain examples, the EMR data 402 may be considered in conjunction with ADT system data 404 and/or caregiver call system data 408. For example, the ADT system data 404 may include the locations of patients admitted to the clinical care environment 10 (e.g., assigned patient rooms) and demographic information relating to the patient, which may aid in identifying the violent individual. In another example, the ADT system data 404 and/or the caregiver call system data 408 may include information relating to negative interactions between patients P and caregivers C, including threats that were made, or altercations that occurred.

The identification factors 900 can include criminal records 908 of an individual. The detection system 122 can perform at least one criminal background check and analyze criminal records associated with an individual who is admitted to the clinical care environment 10 or who is visiting the clinical care environment 10. The detection system 122 can analyze the criminal records to determine whether the individual committed any previous violent crimes (including shootings). Patients P or caregivers C with a history of violent crimes may be more likely to exhibit violent behavior.

The identification factors 900 can include identifying threatening language, tones of voice, or behavior 910 from an individual. In certain examples, this may include verbal threats that are made, an individual raising their voice when speaking, or an individual making a physically threatening posture (e.g., raising their fists into the air). Threatening language, tones of voice, or behavior 910 can be recorded using the audio system 126 and/or the camera system 128. The audio system data 410 and the camera system data 412 containing the threatening language, tones of voice, or behavior 910 can be analyzed by the detection system 122 to identify the threatening language, tones of voice, or behavior 910.

The identification factors 900 can include a weapon identification 912. In certain examples, the camera system 128 can record the camera system data 412 of an individual holding a weapon and transmit the camera system data 412 to the detection system 122. The detection system 122 can then identify, based its analysis of the camera system data 412, that the individual is holding a weapon and what kind of weapon the individual is holding. In certain examples, the detection system 122 can also consider other types of the input data 400 when identifying the weapon (e.g., if audio system data 410 includes loud noises that the detection system 122 determines to be a gunshot).

In some examples, a confidence rating is determined based on one or more of the identification factors 900. The confidence rating relates a likelihood that an individual is properly identified as exhibiting violent behavior. The detection system 122 analyzes data collected by the clinical care environment systems 100 to determine whether an individual exhibits the one or more of the identification factors 900. A higher confidence rating is generated when the detection system 122 determines that more than one of the one or more identification factors 900 are exhibited by a given individual in the clinical care environment 10. A lower confidence rating is generated when the detection system 122 determines fewer of the one or more identification factors 900 are exhibited by a given individual in the clinical care environment 10.

Figure 10:
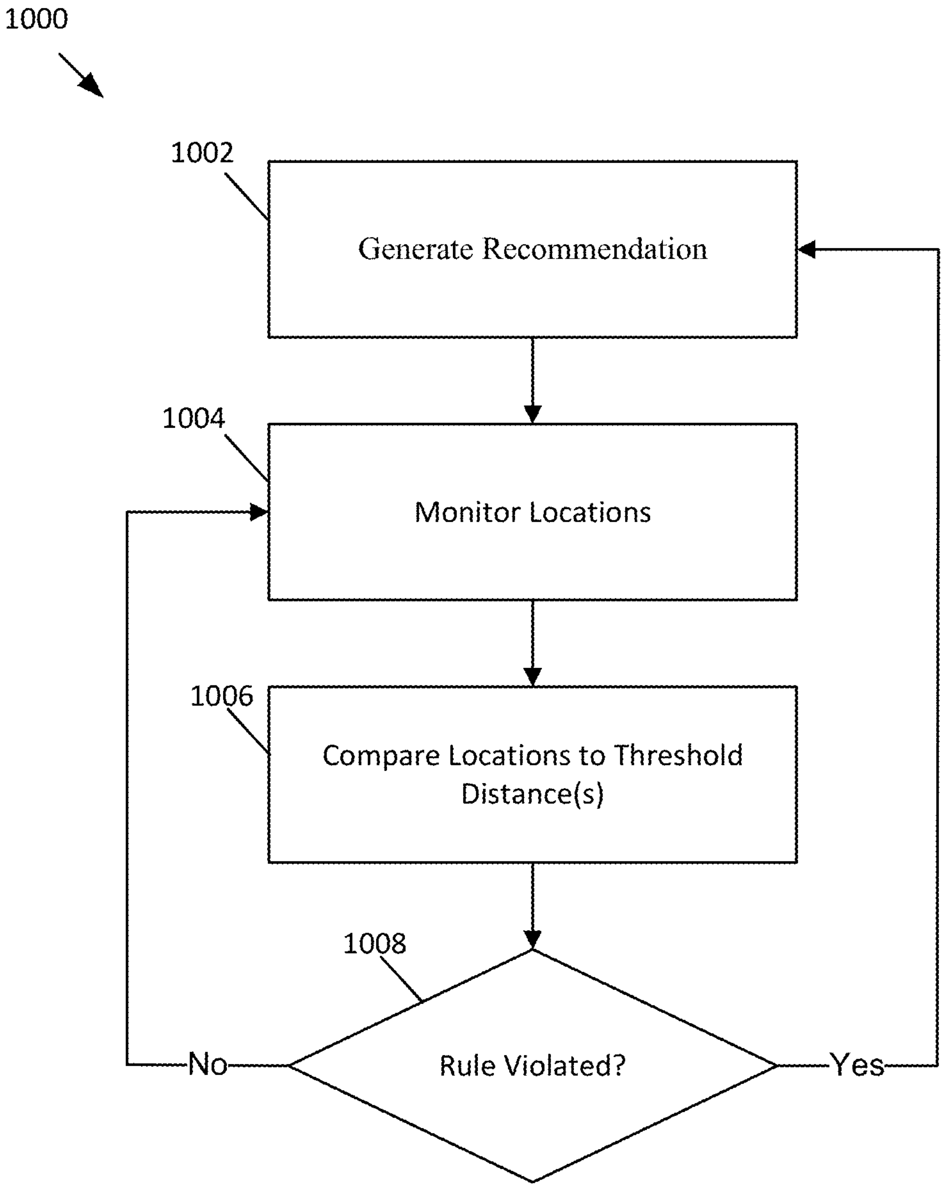
FIG. 10 illustrates an example of a method of generating a recommendation that can be performed by the detection system of FIG. 1.

FIG. 10 illustrates an example of a method 1000 of generating a recommendation that can be performed by the detection system 122. The method 1000 includes a step 1002 of generating the recommendation. The recommendation generated in step 1002 can include an exit path 616 and/or a safe room path 626, such as those shown in FIG. 6. The exit path 616 can be generated by comparing the current location 610 of the user to the locations of one or more exits 608, and the location of the individual who is exhibiting the violent behavior. The safe room path 626 can be generated by comparing the current location 610 of the user to the locations of one or more safe rooms 606, and the location of the individual who is exhibiting the violent behavior.

The method 1000 includes a step 1004 of monitoring locations of individuals in the clinical care environment 10 relative to the exit path 616 and/or the safe room path 626. For example, step 1004 can include monitoring the location of a user of the communications device 102, the locations of other non-violent individuals, and the locations one or more violent individuals relative to the exit path 616 and/or the safe room path 626.

The method 1000 includes a step 1006 of comparing the locations monitored in step 1004 to one or more threshold distances. For example, step 1006 can include comparing the locations of the other non-violent individuals to a first threshold distance from the exit path 616 and/or the safe room path 626. As another example, step 1006 can include comparing the locations of the one or more violent individuals to a second threshold distance from the exit path 616 and/or the safe room path 626. In some examples, the first and second threshold differences are different. For example, the second threshold distance can be larger than the first threshold distance. In other examples, the first and second threshold distances are the same.

The method 1000 includes a step 1008 of determining whether one or more rules are violated based on the comparison of the locations to the one or more threshold distances in step 1006. As an example, a rule can specify a maximum quantity of non-violent individuals that are permitted to be within the first threshold distance of the exit path 616 and/or the safe room path 626. This can avoid overcrowding of non-violent individuals which can prevent a user such as a caregiver or a patient P from safely reaching a safe room 606 or an exit 608. As another example, a rule can specify that the locations of the one or more violent individuals are not permitted to be within the second threshold distance to avoid the user from encountering the one or more violent individuals while following the exit path 616 and/or the safe room path 626 to safety.

When at least one of the one or more rules is violated (i.e., "Yes" in step 1008), the method 1000 returns to step 1002 to generate a new recommendation that includes updates to the exit path 616 and/or the safe room path 626 based on the relative locations of the user of the communications device 102, other non-violent individuals in the clinical care environment 10, the one or more violent individuals, the one or more safe rooms 606, and the one or more exits 608. Otherwise, when the none of the one or more rules are violated (i.e., "No" in step 1008), the method 1000 can return to step 1004 of monitoring the locations of individuals in the clinical care environment 10 relative to the exit path 616 and/or the safe room path 626.

Figure 11:
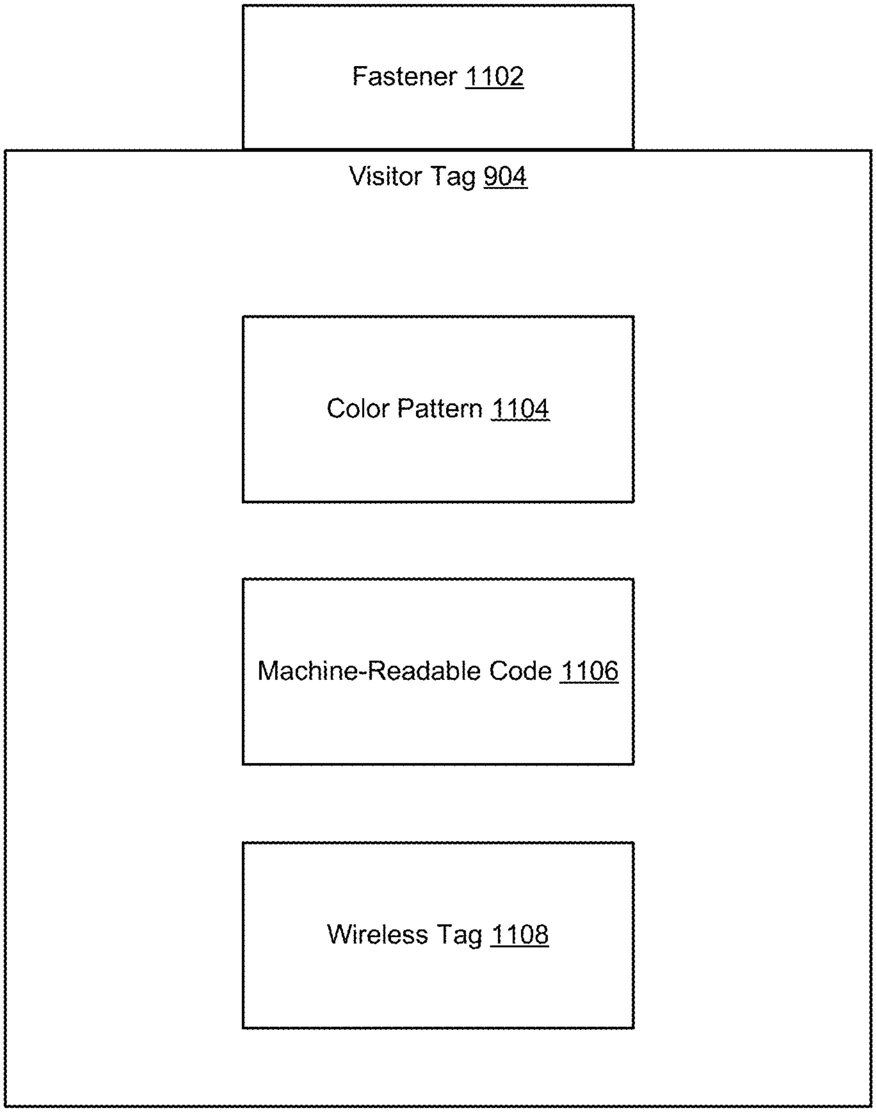
FIG. 11 illustrates an example of a visitor tag that can be used to identify individuals within the clinical care environment of FIG. 1.

FIG. 11 illustrates an example of a visitor tag 904 that can be used by the detection system 122 to identify and track visitors within the clinical care environment 10. The visitor tag 904 can include one or more color patterns 1104 for uniquely identifying individuals based on a perceived threat level or likelihood that the individuals will exhibit violent behavior. Furthermore, the visitor tag 904 can include a machine-readable code, such as a QR code, for discreetly identifying individuals that are more likely to exhibit violent behavior. In certain examples, the machine-readable code 1106 is read by one or more cameras of the camera system 128 for detection by the detection system 122. The detection system 122 can discreetly provide an alert and/or recommendation to a caregiver C who interacts with the individual wearing the visitor tag 904. Further yet, the visitor tag 904 can include a wireless tag 1108 for tracking the location of visitors using the RTLS 110, especially visitors who are determined to have an elevated threat level or likelihood of exhibiting violent behavior. In some examples, the wireless tag 1108 is a radio-frequency identification (RFID) tag. The visitor tag 904 can be coupled to a visitor using a fastener 1102 such as a pin back, a magnetic fastener, a clip fastener, an adhesive backing, a lanyard, a tag holder, Velcro, and the like.

The systems and methods described herein provide significant technical advantages. For example, the detection system 122 improves the efficiency of emergency systems by automatically generating alerts more quickly and efficiently to inform patients P and caregivers C of a violent event. Also, the detection system 122 is a practical application in healthcare technology that conveys specific alerts and/or recommendations, which may include graphical and/or visual information, in a specific way at a communications device 102 to assist caregivers C and patients P. Further yet, the detection system 122 analyzes input data to provide recommendations that improve the safety of patients P and caregivers C. Still further yet, the detection system 122 may automatically implement one or more recommendations such as to manipulate locks, illuminate patient call lights, activate speakers positioned on a patient bed, and other patient devices within a clinical care environment 10.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless of whether shown and described in combination or separately, the various features (both structural and methodological) are intended to be selectively included or omitted to produce an embodiment with a particular set of features.

Having been provided with the description and illustration of the present application, one skilled in the art may envision variations, modifications, and alternate embodiments falling within the spirit of the broader aspects of the claimed inventions and the general inventive concepts embodied in this application that do not depart from the broader scope.

The various embodiments described above are provided by way of illustration only and should not be construed to be limiting in any way. Various modifications can be made to the embodiments described above without departing from the true spirit and scope of the disclosure.

What is claimed is:

1. A system for mitigating violence in a clinical care environment, the system comprising:

at least one processing device; and a memory device storing instructions which, when executed by the at least one processing device, cause the at least one processing device to:

detect at least one individual who is exhibiting violent behavior within the clinical care environment;

identify a location of the at least one individual who is exhibiting the violent behavior based on data received from a location tracking system;

control operation of a first device based on the location of the at least one individual who is exhibiting the violent behavior, the first device being a speaker communicatively coupled to a patient bed located within the clinical care environment, the speaker issuing an audible notification for a patient admitted to the patient bed to remain in the patient bed; and generate an alert based on the location of the at least one individual who is exhibiting the violent behavior, the alert being communicated to a second device associated with a caregiver on duty within the clinical care environment.

2. The system of claim 1, further comprising:

a patient call light positioned outside of a patient room, the patient call light being illuminated to visually indicate an escape route away from the at least one individual who is exhibiting the violent behavior.

3. The system of claim 1, further comprising:

a lock that is remotely controlled to prevent entry into a patient room, a unit, or a department within the clinical care environment.

4. The system of claim 1, further comprising:

a tagging device that is configured to attach a tag to the at least one individual who is exhibiting the violent behavior, the tag being recognizable by the location tracking system for tracking the location of the at least one individual who is exhibiting the violent behavior within the clinical care environment.

5. The system of claim 1, wherein the second device displays an exit path, the exit path generated based on a location of the caregiver, the location of the at least one individual who is exhibiting the violent behavior, and a location of one or more exits within the clinical care environment.

6. The system of claim 5, wherein the exit path is updated based on relative changes between the locations of the caregiver, the at least one individual who is exhibiting the violent behavior, and the one or more exits within the clinical care environment.

7. The system of claim 1, wherein the alert displays a distribution of individuals across a visual map of the clinical care environment, the visual map having first visual indicators of locations of one or more exits within the clinical care environment, and a second visual indicator displaying a location of the at least one individual who is exhibiting the violent behavior.

8. The system of claim 7, wherein the alert further includes an exit path displayed within the visual map, the exit path being calculated based on a minimum distance between the caregiver and an exit of the one or more exits within the clinical care environment.

9. The system of claim 8, wherein the instructions, when executed by the at least one processing device, further cause the at least one processing device to:

compare the exit path to the location of the at least one individual who is exhibiting the violent behavior;

calculate a distance between the exit path and the location of the at least one individual who is exhibiting the violent behavior;

compare the distance to a threshold value; and modify the exit path when the distance is less than the threshold value.

10. The system of claim 8, wherein the instructions, when executed by the at least one processing device, further cause the at least one processing device to:

calculate a number of individuals within a threshold distance from the exit path;

compare the number of individuals within the threshold distance from the exit path to a threshold value; and modify the exit path when the number of individuals within the threshold distance from the exit path exceeds the threshold value.

11. The system of claim 1, wherein the instructions, when executed by the at least one processing device, further cause the at least one processing device to:

receive audio system data from an audio system;

analyze the audio system data to identify threatening language, tones, or behaviors; and detect the at least one individual who is exhibiting the violent behavior based on the threatening language, tones, or behaviors.

12. The system of claim 1, wherein the instructions, when executed by the at least one processing device, further cause the at least one processing device to:

generate a confidence rating relating to a confidence of correctly identifying the at least one individual who is exhibiting violent behavior based on one or more identification factors.

13. The system of claim 1, wherein the alert includes a distribution of safe rooms across a visual map of the clinical care environment, wherein the visual map includes at least one safe room path for guiding the caregiver to the safe room.

14. The system of claim 1, wherein the instructions, when executed by the at least one processing device, further cause the at least one processing device to:

track the location of the at least one individual who is exhibiting the violent behavior by coupling a tag to the at least one individual who is exhibiting the violent behavior and tracking the location of the tag;

wherein the tag is coupled to the at least one individual who is exhibiting the violent behavior by firing a projectile; and wherein the projectile is fired from a tagging device fixed in a location within the clinical care environment.

15. The system of claim 1, wherein the instructions, when executed by the at least one processing device, further cause the at least one processing device to:

generate the alert when at least one of threatening language, tones, or behaviors are identified based on data captured by at least one of an audio system and a camera system located within the clinical care environment.

16. A method of mitigating violence in a clinical care environment, the method comprising:

detecting at least one individual who is exhibiting violent behavior within the clinical care environment;

identifying a location of the at least one individual who is exhibiting the violent behavior based on data received from a location tracking system;

controlling operation of a first device based on the location of the at least one individual who is exhibiting the violent behavior, the first device being a speaker communicatively coupled to a patient bed located within the clinical care environment, the speaker issuing an audible notification for a patient admitted to the patient bed to remain in the patient bed; and generating an alert based on the location of the at least one individual who is exhibiting the violent behavior, the alert being communicated to a second device associated with a caregiver on duty within the clinical care environment.

17. The method of claim 16, further comprising:

illuminating a patient call light to identify an escape route away from the at least one individual who is exhibiting the violent behavior.

18. The method of claim 16, further comprising:

operating a tagging device to attach a tag to the at least one individual who is exhibiting the violent behavior, the tag being recognizable by the location tracking system for tracking the location of the at least one individual who is exhibiting the violent behavior within the clinical care environment.

* * * * *